United States Patent [19]
Mark et al.

[11] Patent Number: 4,737,462
[45] Date of Patent: Apr. 12, 1988

[54] STRUCTURAL GENES, PLASMIDS AND TRANSFORMED CELLS FOR PRODUCING CYSTEINE DEPLETED MUTEINS OF INTERFERON-β

[75] Inventors: David F. Mark, Hercules; Leo S. Lin, Fremont; Shi-Da Yu Lu, Oakland, all of Calif.

[73] Assignee: Cetus Corporation, Emeryville, Calif.

[21] Appl. No.: 753,717

[22] Filed: Jul. 10, 1985

Related U.S. Application Data

[63] Continuation of Ser. No. 435,154, Oct. 19, 1982, abandoned.

[51] Int. Cl.$^4$ .................. C12N 1/20; C12N 15/00; C07H 21/04
[52] U.S. Cl. .................. 435/253; 435/240.2; 435/240.1; 435/240.4; 435/320; 435/253; 435/243; 536/27; 424/85
[58] Field of Search .................. 536/27–29; 435/317, 253, 240.2, 240.1, 240.4, 320, 243; 424/85

[56] References Cited

U.S. PATENT DOCUMENTS 4,414,150  11/1983  Goeddel .................. 424/85

FOREIGN PATENT DOCUMENTS 0028033  5/1981  European Pat. Off. .
0042246  12/1981  European Pat. Off. .
0041313  12/1981  European Pat. Off. .
0128467  12/1984  European Pat. Off. .
2063882  6/1981  United Kingdom .

OTHER PUBLICATIONS

Shepard, H. Michael, et al., Nature, vol. 294, pp. 563–565, (1981).
Taniguchi, T. et al., Gene, vol. 10, pp. 11–15 (1980).
Knight, E., Jr. et al., Journal of Interferon Research, (1982), vol. 2, No. 3, pp. 421–429.
Allen, G. et al., Nature (1981), 78(10) 6186–6190.
Rieger, R. et al., Glossary of Genetics and Cytogenetics, p. 381.
Taniguchi, T. et al., Nature, vol. 285, pp. 547–549 (1980).
Lathe, R. F., et al., Genetic Engineering, pp. 30–51.
Smith, M. and Gillam, S. Constructed Mutants Using Synthetic Oligodeoxyribonucleotides as Site-Specific Mutagens-Department of Biochemistry, Faculty of Medicine University of British Columbia.
Goeddel, D. V. et al., Nucleic Acids Research, vol. 8 No. 18, pp. 4059–4075.
Taniguchi, T. et al., Proc. Natl. Acad. Sci vol. 77, No. 9, pp. 5230–5233 (1980).
Allen, G. et al., Nature., vol. 287 (1980), pp. 408–411.
Levy, W. P., et al., Proc. Natl. Acad. Sci., vol. 78, No. 10, pp. 6186–6190 (1981).
Rastetter, W. H., Trends in Biotechnology, vol. 1, No. 3 (1983).
Goeddel, D. V., et al., Nature, vol. 287, pp. 411–416 (1980).
Derynck, R. et al., Nature vol. 287, pp. 193–197, (1980).
Derynck, R., et al., Nature vol. 285, pp. 542–546, (1980).
Stewart, A. G., et al., Nucleic Acids Research, vol. 8, pp. 1913–1931 (1980).

Primary Examiner—Blondel Hazel
Attorney, Agent, or Firm—Shyamala T. Rajender; Albert P. Halluin

[57] ABSTRACT

A modified IFN-β is provided wherein the cysteine residue at position 17 is deleted and serine is substituted therefor. DNA sequences coding for the modified protein, nucleotide primers used for the mutagenesis, appropriate cloning vectors, host organisms transformed with the vectors, methods for the production and use of the modified IFN-β (IFN-$β_{ser17}$) are also provided. The specific activity of IFN-$β_{ser17}$ is found to be substantially the same as that of native IFN-β.

15 Claims, 9 Drawing Sheets

```
                    5                   10                  15                  20
MetSerTyrAsnLeu LeuGlyPheLeuGln ArgSerSerAsnPhe GlnCysGlnLysLeu
                    25                  30                  35                  40
LeuTrpGlnLeuAsn GlyArgLeuGluTyr CysLeuLysAspArg MetAsnPheAspIle
                    45                  50                  55                  60
ProGluGluIleLys GlnLeuGlnGlnPhe GlnLysGluAspAla AlaLeuThrIleTyr
                    65                  70                  75                  80
GluMetLeuGlnAsn IlePheAlaIlePhe ArgGlnAspSerSer SerThrGlyTrpAsn
                    85                  90                  95                  100
GluThrIleValGlu AsnLeuLeuAlaAsn ValTyrHisGlnIle AsnHisLeuLysThr
                   105                 110                 115                 120
ValLeuGluGluLys LeuGluLysGluAsp PheThrArgGlyLys LeuMetSerSerLeu
                   125                 130                 135                 140
HisLeuLysArgTyr TyrGlyArgIleLeu HisTyrLeuLysAla LysGluTyrSerHis
                   145                 150                 155                 160
CysAlaTrpThrIle ValArgValGluIle LeuAgAsnPheTyr  PheIleAsnArgLeu
                   165                 170                 175                 180
ThrGlyTyrLeuArg Asn---
```

FIG. 1

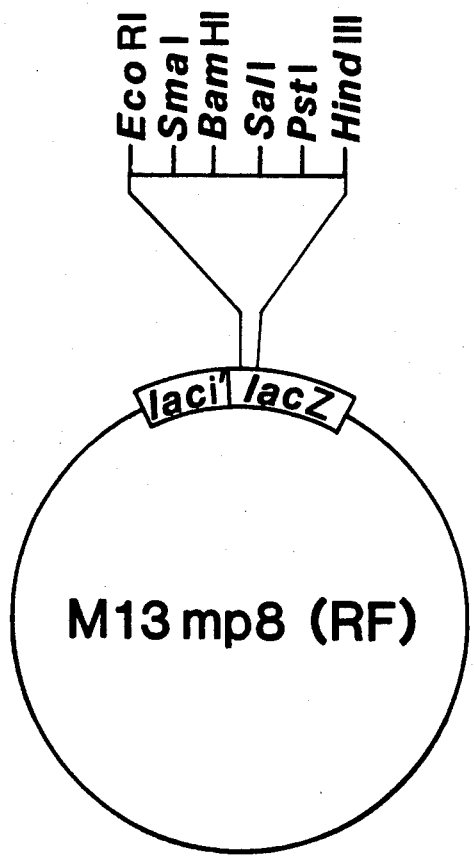

FIG. 4

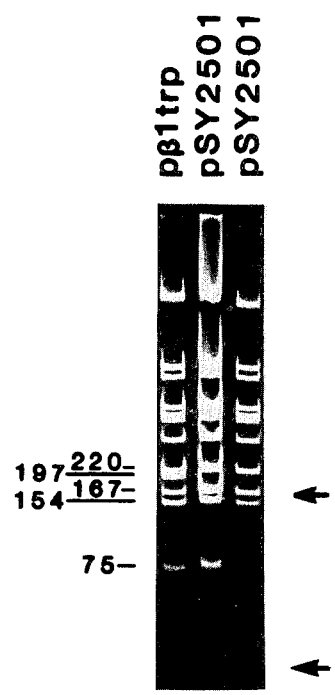
FIG. 8a
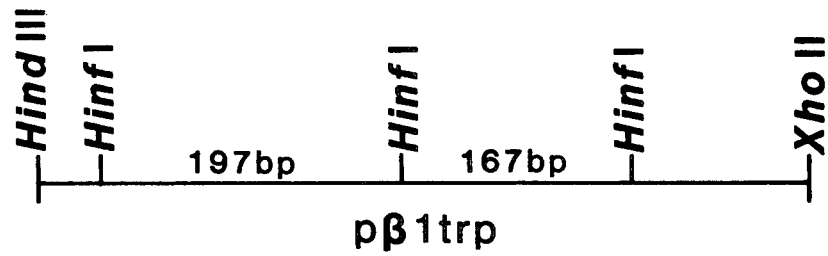
pβ1trp
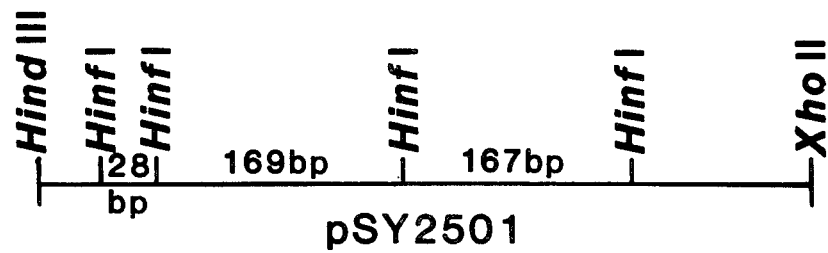
pSY2501

IFN-B CYS TO SER CHANGE AT AMINO ACID 17

```
1                                                                17
ATG AGC TAC AAC TTG CTT GGA TTC CTA CAA AGA AGC AGC AAT TTT CAG AGT  CAG AAG CTC
met ser tyr asn leu leu gly phe leu gln arg ser ser asn phe gln ser  gln lys leu 61
CTG TGG CAA TTG AAT GGG AGG CTT GAA TAT TGC CTC AAG GAC AGG ATG AAC TTT GAC ATC
leu trp gln leu asn gly arg leu glu tyr cys leu lys asp arg met asn phe asp ile 121
CCT GAG GAG ATT AAG CAG CTG CAG CAG TTC CAG AAG GAG GAC GCC GCA TTG ACC ATC TAT
pro glu glu ile lys gln leu gln gln phe gln lys glu asp ala ala leu thr ile tyr 181
GAG ATG CTC CAG AAC ATC TTT GCT ATT TTC AGA CAA GAT TCA TCT AGC ACT GGC TGG AAT
glu met leu gln asn ile phe ala ile phe arg gln asp ser ser ser thr gly trp asn 241
GAG ACT ATT GTT GAG AAC CTC CTG GCT AAT GTC TAT CAT CAG ATA AAC CAT CTG AAG ACA
glu thr ile val glu asn leu leu ala asn val tyr his gln ile asn his leu lys thr 301
GTC CTG GAA GAA AAA CTG GAG AAA GAA GAT TTC ACC AGG GGA AAA CTC ATG AGC AGT CTG
val leu glu glu lys leu glu lys glu asp phe thr arg gly lys leu met ser ser leu 361
CAC CTG AAA AGA TAT TAT GGG AGG ATT CTG CAT TAC CTG AAG GCC AAG GAG TAC AGT CAC
his leu lys arg tyr tyr gly arg ile leu his tyr leu lys ala lys glu tyr ser his 421
TGT GCC TGG ACC ATA GTC AGA GTG GAA ATC CTA AGG AAC TTT TAC TTC ATT AAC AGA CTT
cys ala trp thr ile val arg val glu ile leu arg asn phe tyr phe ile asn arg leu 481
ACA GGT TAC CTC CGA AAC TGA AGA TC
thr gly tyr leu arg asn ***
```

FIG. 10

STRUCTURAL GENES, PLASMIDS AND TRANSFORMED CELLS FOR PRODUCING CYSTEINE DEPLETED MUTEINS OF INTERFERON-β

This is a continuation of application Ser. No. 06/435,154, filed Oct. 19, 1982, now abandoned.

This invention is in the general area of recombinant DNA technology. More specifically, it relates to a microbially produced, modified human fibroblast interferon, DNA sequences which encode the modified protein, cloning vectors incorporating the DNA sequences, host organisms transformed with the vectors and therapeutic formulations including the modified human fibroblast interferon.

Interferons are relatively small, single chain polypeptide proteins which are secreted by most animal cells in response to exposure to a variety of inducers such as, for example, viruses, mitogens and polynculeotides. Because of their antiviral, antiproliferative and immunomodulatory properties, interferons are of great interest as therapeutic agents. They have shown promising results in clinical tests in the treatment of viral diseases and cancer. (J. Desyter et al., Lancet 11, 645-647 (1976); R. Derynck et al., Nature 287, 193 (1980)). Although interferons were discovered nearly twenty five years ago, it is only in recent times with the advent of recombinant DNA (rDNA) technology, that the structure of the genes and of the proteins are being elucidated. Studies of the structures and properties of interferons (IFNs) and clinical studies using IFNs as therapeutic agents thus far have been severely limited by the small amounts of pur material available.

Human IFNs are classified into three major types, α, β and γ, IFN-α being produced by leukocytes, IFN-β by fibroblasts and IFN-γ by the immune system. Although IFN-α and IFN-β have been shown to be serologically distinguishable (R. L. Cavalieri, Proc. Natl. Acad. Sci., 74, 3287 (1977)), the two interferon types have several features in common: they are both polypeptides consisting o about 165 amino acid residues in the molecular weight range of 16,000 to 26,000 daltons, their synthesis is under similar cellular control and the responses elicited in target cells are similar (T. Taniguchi et al., Nature 285, 547 (1980)). Taniguchi et al., supra, reported that the nucleotide sequences of the two types of IFNs show an average homology of 3% in the domain of the signal sequence and of 45% in the IFN polypeptide sequence. This was confirmed by R. Derynck, Nature, 285, 542-547 (1980).

Naturally produced or native IFN-β has been purified to homogeneity as a single chain polypeptide of 19,000 to 20,000 dalton molecular weight with a specific activity (antiviral) of $2 \times 10^8$ units/mg protein (E. Knight, Jr., Proc. Natl. Acad. Sci., 73, 520-523 (1976); W. Berthold, J. Biol. Chem., 253, 5206 (1978)). The sequence of the thirteen $NH_2$-terminal amino acids of IFN-β has been determined (E. Knight, Jr., et al., Science, 207, 525-526 (1980)). Using synthetic deoxyoligonucleotides predicted from the amino acid sequence of the $NH_2$-terminus, Houghton et al., (Nuc. Acids Res., 8, 1913-1931 (1980)) determined the sequence of the 276 5' terminal nucleotides of IFN-62 mRNA. Taniguchi et al., (Proc. Japan Acad. 855, 464-469 (1979)) and Derynck et al., (Nature, 285, 542-547 (1980)) employed selection procedures to identify cloned cDNA copies of IFN-β mRNA in E. coli. D. V. Goeddel et al., (Nuc. Acids Res. 8, 4057 (1980)), using a battery of synthetic DNA primers designed from published amino acid sequence data, were able to identify bacterial clones containing IFN-β cDNA sequences.

Although at least some IFNs are believed to be glycoproteins, IFN-β is the only interferon that has been shown to be a glycoprotein by chemical measurement of its carbohydrate content. It has one N-glycosidyl attachment site (E. Knight, Jr., Proc. Natl. Acad. Sci., 73, 520 (1976)., E. Knight, Jr., and D. Fahey, J. Interferon Res., 2 (3), 421 (1982)). Even though not much is known about the kinds of sugars which make up the carbohydrate moiety of IFN-β or where they are attached to the protein, it has been shown that the carbohydrate moiety is not essential for its antigenicity, biological activity or hydrophobicity. (Taniguchi et al., supra; E. Knight, Jr. and E. Knight, Jr. and D. Fahey, supra). The gene for IFN-β has been cloned and expressed in E. coli, which has no mechanism for attachment of carbohydrates to proteins. The IFN-β produced in E. coli by rDNA technology, has in vitro viral activity similar to that of native IFN-β indicating that glycosylation is not essential for activity. The nucleotide sequence and the deduced amino acid sequence of IFN-β published by Taniguchi, et. al., (Gene 10, 11-15 (1980)) and R. Derynck, et al., supra, show that there are three cysteine (cys) residues in IFN-β at amino acid positions 17, 31 and 141. Cys 141 has been shown to be essential for preserving the antiviral activity of IFN-β (H. M. Shepard et. al., Nature 294, 563 (1981)). IFN-α have been shown to contain four cysteine (cys) residues at positions 1, 29, 98 and 138 of the polypeptide chain (W. P. Levy et al., Proc. Natl. Acad. Sci., 78, 6186 (1981)), with residues 1 and 98 and residues 29 and 138 believed to be linked by disulfide bridges (N. Stebbing et al., "The Biology of the Interferon System", Eds. E. De Meyer et al., Elsevier Press (1981)).

European Patent Application No. 81301414.9 discloses DNA sequences, rDNA molecules and processes for producing human fibroblast interferon like polypeptides. Japanese Application corresponding to U.S. Ser. No. 201,359 teaches DNA and plasmid for the production of human fibroblast interferon.

In the course of the preparation of IFN-β by rDNA techniques, it has been observed that dimers and oligomers of microbially produced IFN-β are formed in E. coli extracts containing high concentrations of IFNβ. This multimer formation renders purification and separation IFN-β very laborious and time consuming and necessitate several additional steps in the purification and isolation procedures such as reducing the protein during purification and reoxidizing it to restore it to the original conformation, thereby increasing the possibility of incorrect disulfide bond formation. Furthermore, microbially produced IFN-β has also been found to exhibit consistently low specific activity due perhaps to the formation of multimers or of random disulfide bridges.

It would be desirable therefore to be able to obtain by rDNA techniques, IFN-β in a monomeric form which retains the specific activity substantially that of native IFN-β, and which would facilitate the isolation and purification of the protein product.

Accordingly, the principal object of the present invention is to provide single or multiple site-specific and sitedirected substitutions and mutations in the IFN-β gene.

Another object of the present invention is to provide IFN-β with no free sulfhydryl groups present.

A further object is to provide a modified IFN-β with only two cysteine residues.

Another object of the instant invention is to provide IFN-β which would be substantially in the monomeric form.

Yet another object is to provide a method for single or multiple site-specific and site-directed mutations in the IFN-β gene.

Another object is to provide interferon therapy including the products produced in accordance with the present invention.

Still another object is to provide modified IFN-β which exhibits specific activity close to that of native IFN-β.

A further object is to provide a IFN-β where cys 17 is deleted and serine is substituted therefor.

Additional objects, advantages and novel features of the invention will be set forth in part in the description which follows, and in part will become apparent to those skilled in the art upon examination of the following or may be learned by practice of the invention. The objects and advantages may be attained by means of the instrumentalities and combinations particularly pointed out in the appended claims.

SUMMARY OF THE INVENTION

To achieve the foregoing and other objects and in accordance with the purpose of the present invention, as embodied and broadly described herein, one aspect of the invention provides site-specific and site-directed single or multiple mutations in the DNA sequence of the IFN-β gene, or cDNA.

Another aspect of the instant invention provides a method for site-specific and site-directed single or multiple mutations in the DNA sequence of the IFN-β gene, or cDNA.

Yet another aspect of the instant invention involves a single, predetermined, site-specific and site-directed mutation in the DNA sequence coding for the mature IFN-β.

In one preferred embodiment of the invention as described and claimed herein, the TGT codon at position 17 of the coding sequence for the mature IFN-β is modified to an AGT codon, thereby replacing the cysteine (cys) at position 17 of the amino acid sequence with a serine. This modification eliminates a free —SH group which may be contributing to the formation of oligomers of IFN-β or to the formation of random, incorrect disulfide links which could alter the protein conformation and thereby its specific activity. As used herein, IFN-β includes native, rDNA produced, synthetic or semisynthetic human fibroblast interferons and interferon-like Polypeptides.

The method for preparing the modified IFN-β broadly involves isolating human IFN-β gene and inducing therein a site-specific mutagenesis at codon 17 using a synthetic 17-nucleotide primer GCAATTTT-CAGAGTCAG which includes an AGT codon for serine. The nomenclature and designation of bases is conventional and is well known in the art. The T→A point mutation results in changing a cysteine to a serine. The primer is then hybridized to single stranded M13 phage DNA which contains the sense strand for the IFN-β gene. The phage DNA is then made double-stranded by reaction with DNA polymerase I Klenow fragment. The T→A mutation results in the creation of a nucleotide sequence corresponding to a new HinfI restriction site in the IFN-β gene which facilitates the screening process for the mutated clone. The cloning vector is then inserted in an expression plasmid and a suitable host organism transformed with the cloning vector. The host organism produces the mature IFN-β with the cysteine at position 17 changed to serine. This modified IFN-β is hereinafter designated as IFN-$\beta_{ser17}$. The protein is then extracted, isolated, purified and characterized.

In another aspect of the present invention, therapeutic formulations, which include effective amounts of IFN-$\beta_{ser17}$, are provided for treatment of viral infections, various types of cancer and other pathological conditions where interferon therapy is indicated.

BRIEF DESCRIPTION OF THE DRAWINGS

FIG. 1 is a diagram of the amino acid sequence of IFN-β.

FIG. 4 is a diagram of the cloning vector M13mp8 phage.

FIG. 8a shows the HinfI restriction pattern of clone pSY2501 and FIG. 8b shows the resulting two 169bp and 28bp fragments thereof.

FIG. 10 shows the coding DNA sequence for mature IFN-$\beta_{ser17}$ with the corresponding amino acid sequence.

DESCRIPTION OF THE INVENTION

Figure 2:
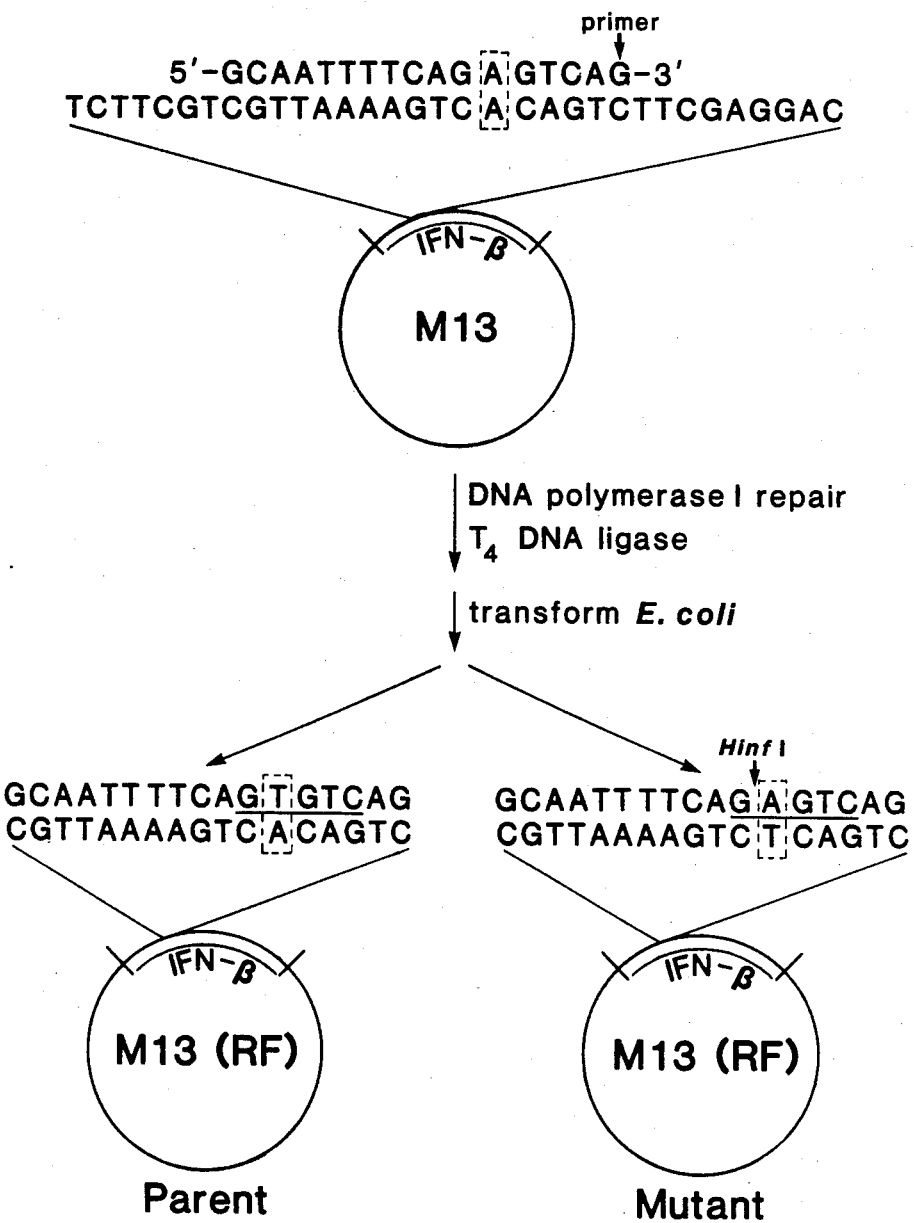
FIG. 2 is a schematic illustration showing the hybridization of the nucleotide primer with IFN-β gene.

The present invention provides: IFN-β wherein the cysteine at position 17 is deleted and serine is substituted therefor; DNA fragments coding for the modified protein; nucleotide primers used for the mutagenesis; appropriate cloning vectors; transformed host organisms which produce the protein; method for their production; and therapeutic formulations for the use of IFN-$\beta_{ser17}$ as a therapeutic agent.

It has been shown by Taniguchi et al., and by Derynck et al., supra, that both the glycosylated and unglycosylated IFNs show qualitatively similar specific activities and that, therefore, the glycosyl moieties are not involved in and do not contribute to the biological activity of IFN-β. However, bacterially produced IFN-β which is unglycosylated consistently exhibits quantitatively lower specific activity than native IFN-β which is glycosylated. IFN-β is known to have three cysteine residues at positions 17, 31 and 141. Cysteine 141 has been demonstrated by Shepard et al., supra, to be essential for biological activity. In IFN-αs, which contain four cysteine residues, there are two —S—S— bond between cys 29 and cys 138 and between cys 1 and cys 98. By analogy, the cys 141 of IFN-β could be involved in an —S—S— bond with cys 31, leaving a free —SH group on cys 17. The consistently lower specific activity observed with the microbially produced IFN-β could, therefore, be due to either intermolecular aggregation through a free —SH group of one of the three cys residues or to the random formation of a mixture of incorrect and correct intramolecular disulfide links involving cys 17,31 and 141. If cys 17 is substituted by a different amino acid to remove at least one free —SH group, such a transformation is likely to provide some valuable information as to the possible involvement of cys 17 in biological activity; its role in the possible formation of incorrect intramolecular —S—S— bonds between cys 17 and cys 31 or between cys 17 and cys 141 which might affect the biological activity; and its role in the formation of multimers through intermolecular disulfide bonds. If cys 17 is not essential for the biological activity of the protein, the resulting cysdeleted protein might then exhibit specific activity close to that of native IFN-β and would possibly also facilitate isolation and purification of the protein.

By the use of appropriate, synthetic oligonucleotide primers containing single or multiple or a plurality of base changes, coding for a given amino acid, cys 17 or any other amino acid of choice may be transformed to other amino acids. Conversion of cys 17 to neutral amino acids such as glycine, valine, alanine, leucine, isoleucine, tyrosine, phenylalanine, histidine, tryptophan, serine, threonine and methionine is the preferred approach. Serine and threonine are the most preferred replacements for cys 17.

The size of the oligonucleotide primer is determined by the requirement for stable hybridization of the primer to the DNA in which the mutation is to be induced, and by the limitations of the currently available synthetic methods for synthesizing the oligonucleotides. As used herein, mutations include without limitation single or multiple base changes, substitutions, deletions, insertions, inversions and the like. Oligonucleotides used for mutagenesis in accordance with the present invention usually range from about 12 to about 24 bases, preferably from about 14 to about 20 bases and still more preferably from about 15 to about 18 bases.

The method for preparing the modified IFN-β broadly involves isolating human IFN-β gene and inducing therein a site-specific mutagenesis at codon 17 using a synthetic 17-nucleotide primer GCAATTTT-CAGAGTCAG which includes an AGT codon for serine. The nomenclature and designation of bases is conventional and is well known in the art. The T→A point mutation results in changing cysteine to a serine. The primer is then hybridized to single stranded M13 phage DNA which contains the sense strand for the IFN-β gene. The phage DNA is then made double-stranded by reaction with DNA polymerase I Klenow fragment. The T→A mutation results in the creation of a new HinfI restriction site in the IFN-β gene which facilitates the screening process for the mutated clone.

The mutated DNA is then cloned into an appropriate vector such as a bacterial plasmid or λ phage and a host organism transformed with the vector. The host organism then produces the modified IFN-β. Preferred vectors are plasmid pBR322, pCR1, and variants thereof, other host plasmids, M13 phages, and variants thereof, synthetic vectors and the like. Suitable host organisms are E. coli, Pseudomonas, Bacillus subtilis, Bacillus thuringiensis, various strains of yeast, Bacillus thermophilus, animal cells, plant cells, animal and plant hosts and the like. They may be prokaryotic or eukaryotic. E. coli is the preferred transformant. The IFN-$β_{ser17}$ obtained in accordance with the present invention may be glycosylated or unglycosylated depending on the host organism of choice. The unglycosylated protein obtained when E. coli is the host organism, may be optionally glycosylated in vitro by chemical, enzymatic and other types of modifications known in the art.

In one preferred embodiment of the subject invention, the cysteine residue at position 17 in the amino acid sequence of IFN-β, as shown in FIG. 1, is changed to serine by a single base mutation of T→A in codon 17 of the DNA sequence which codes for the mature IFN-β. The site-specific mutagenesis is induced using a synthetic 17-nucleotide primer GCAATTTTCAGAGT-CAG which is complementary to the seventeen nucleotides on the sense strand of IFN-β gene which include the complementary base triplet of the TGT codon 17 for cysteine. There is a one base change at nucleotide 12 in the primer from a T→A to induce the mutation. As used herein and as understood by those skilled in the art, sense strand is the DNA strand of dsDNA which is identical to the message it encodes, while the other strand is complementary thereto.

It must be recognized that the genetic code is degenerate and that many of the amino acids may be encoded by more than one codon. The base code for serine, for example, is sixway degenerate such that the codons TCT, TCG, TCC, TCA, AGT and ACG all code for serine. The AGT codon was chosen for the preferred embodiment for convenience. Similarly, threonine is encoded by any one of codons ACT, ACA, ACC and ACG. It is intended that when a codon is specified for a particular amino acid, it includes all degenerate codons which encode that amino acid.

The 17-base primer is synthesized and hybridized to single stranded M13 phage DNA which carries the sense strand of the IFN-β gene. The phage DNA is then reacted with DNA polymerase I Klenow fragment to convert it into double stranded (ds) DNA, as shown in FIG. 2. The T→A mutation, shown in FIG. 2, results in the creation of a new HinfI restriction site in the IFN-β gene. The mutated clone is identified by using the oligonucleotide primer as a probe in a hybridization screening of the mutated phage plaques. The primer will have a single mismatch near the middle of the primer sequence when hybridized to the parent but will have a perfect match when hybridized to the mutated phage DNA, as indicated in FIG. 2. Hybridization conditions can then be devised where the oligonucleotide primer will preferentially hybridize to the mutated DNA but not to the parent DNA. The newly generated HinfI site also serves as a mean of confirming the single base mutation in the IFN-β gene.

The M13 phage DNA carrying the mutated gene is isolated and spliced into an appropriate expression vector, plasmid pTrp3, and E. coli strain MM294 is transformed with the vector. The expressed protein, IFN-$β_{ser17}$, is isolated, purified and characterized.

The following examples are presented to help in the better understanding of the subject invention and for purposes of illustration only. They are not to be construed as limiting the scope of the invention in any manner or means.

EXAMPLE 1

Cloning Of IFN-β Into M13 Vector

The use of M13 phage vector as a source of singlestranded DNA template has been demonstrated by G. F.

Figure 3:
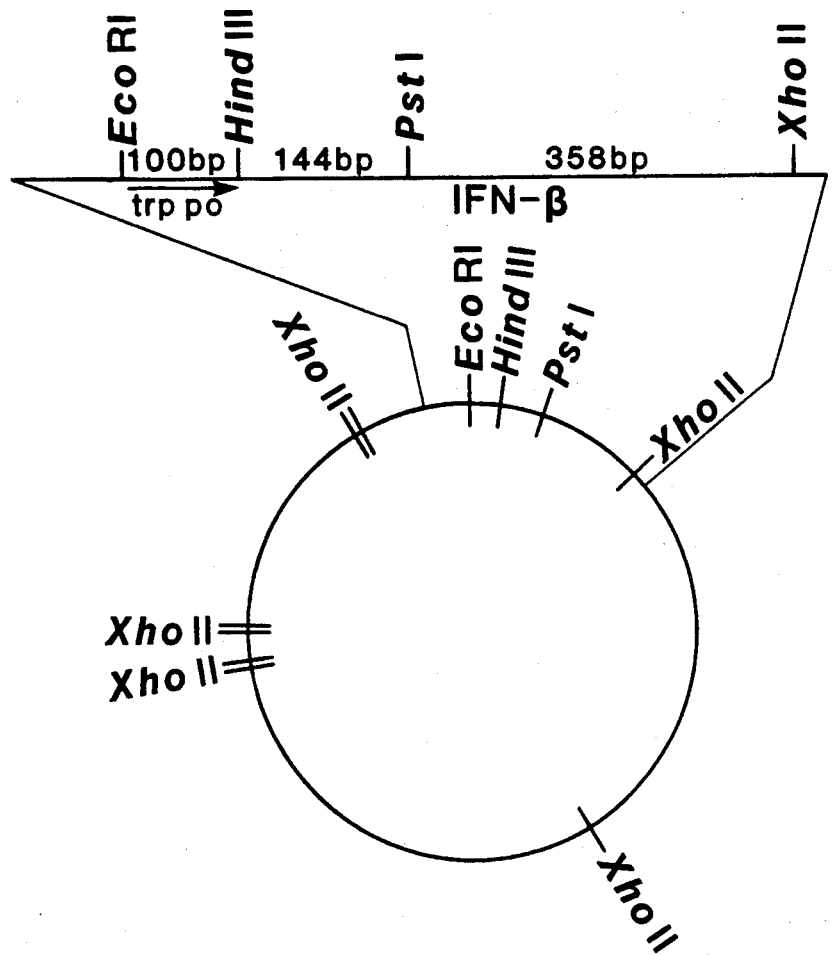
FIG. 3 shows a diagram of plasmid pβ1trp including the IFN-β gene.
Figure 5:
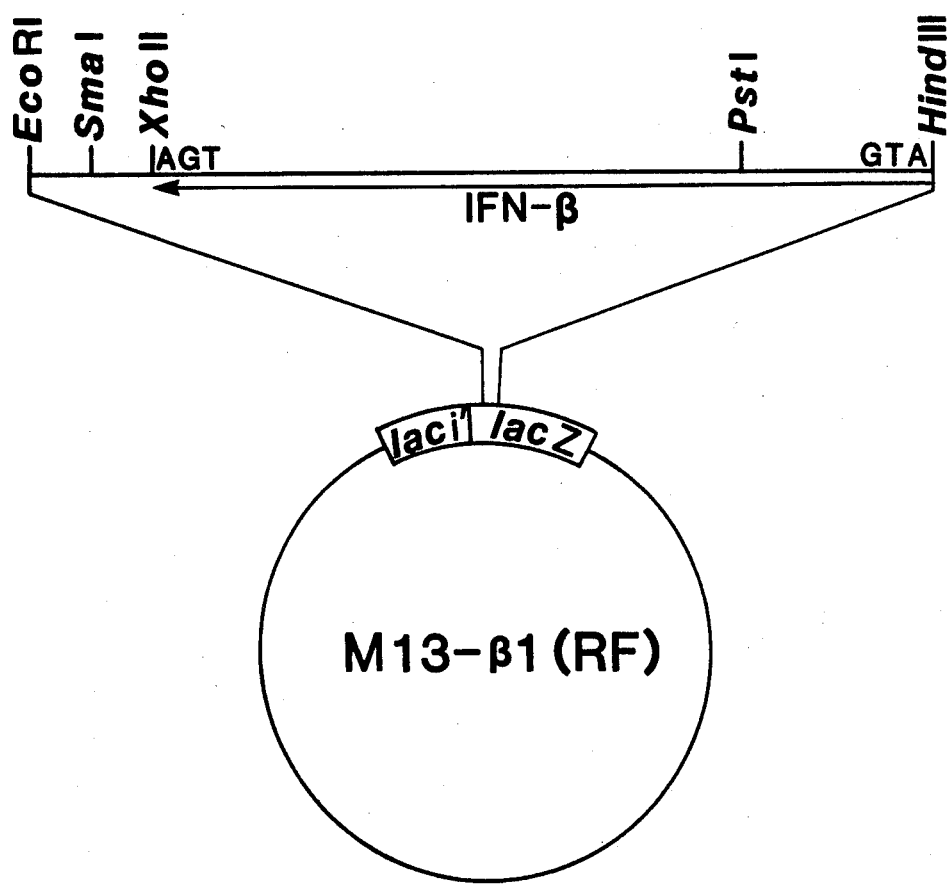
FIG. 5 shows the restriction map of clone M13-β1.

Temple et al., Nature, 296, 537-540 (1982). Plasmid pβ1trp (FIG. 3) containing the IFN-β gene under the control of E. coli trp promoter, was digested with the restriction enzymes HindIII and XhoII. The M13mp8 (J. Messing, "Third Cleveland Symposium on Macromolecules: Recombinant DNA", Ed. A. Walton, Elsevier Press, 143-153 (1981)) replicative form (RF) DNA (FIG. 4) was digested with restriction enzymes HindIII and BamHI, and mixed with the pβ1trp DNA which had previously been digested with HindIII and XhoII. The mixture was then ligated with T4 DNA ligase and the ligated DNA transformed into competent cells of E. coli strain JM103 and plated on Xgal indicator plates (J. Messing et. al., Nucleic Acids Res., 9, 309-321 (1981)). Plaques containing recombinant phage (white plaques) were picked, inoculated into a fresh culture of JM103 and mini-preps of RF molecules prepared from the infected cells (H. D. Birnboim and J. Doly, Nucleic Acid Res. 7, 1513-1523 (1979)). The RF molecules were digested with various restriction enzymes to identify the clones containing the IFN-β insert. The restriction map of one such clone (M13-β1) is shown in FIG. 5. Single-stranded phage DNA was prepared from clone M13-β1 to serve as template for site-specific mutagenesis using a synthetic oligo-nucleotide.

EXAMPLE 2

Site-Specific Mutagenesis

Forty picomoles of the synthetic oligonucleotide GCAATTTTCAGAGTCAG (primer) was treated with T4 kinase in the presence of 0.1 mM ATP, 50 mM Tris-HCl pH 8.0, 10 mM MgCl$_2$, 5 mM DTT and 9 units of T4 kinase, in 50 μl at 37° C. for 1 hour. The kinased primer (12 pmole) was hybridized to 5 μg of single-stranded (ss) M13-β1 DNA in 50 μl of a mixture containing 50 mM NaCl, 10 mM Tris-HCl, pH 8.0, 10 mM MgCl$_2$ and 10 mM β-mercaptoethanol, by heating at 67° C. for 5 min and at 42° C. for 25 min. The annealed mixture was then chilled on ice and then added to 50 μl of a reaction mixture containing 0.5 mM each of dNTP, 80 mM Tris-HCl pH 7.4, 8 mM MgCl$_2$, 100 mM NaCl, 9 units of DNA polymerase I, Klenow fragment, 0.5 mM ATP and 2 units of T4 DNA ligase, incubated at 37° C. for 3 hours and at 25° C. for 2 hours. The reaction was then terminated by phenol extraction and ethanol precipitation. The DNA was dissolved in 10 mM Tris-HCl pH 8.0, 10 mM EDTA, 50% sucrose and 0.05% bromophenylblue and electrophoresed on 0.8% agarose gel in the presence of 2 μg/ml of ethidium bromide. The DNA bands corresponding to the RF forms of M13-β1 were eluted from gel slices by the perchlorate method (R. W. Davis et al., "Advanced Bacterial Genetics", Cold Spring Harbor Laboratory, N. Y., p. 178-179 (1980)). The eluted DNA was used to transform competent JM103 cells, grown over-night and single-stranded DNA isolated from the culture supernatant. This ssDNA was used as a template in a second cycle of primer extension as described above. After completion of the second cycle of primer extension, the gel purified RF forms of the DNA were transformed into competent JM103 cells, plated onto agar plates and incubated overnight to obtain phage plaques.

EXAMPLE 3

Screening And Identification Of Mutagenized Plaques

Plates containing mutated M13-β1 plaques as well as two plates containing unmutated M13-β1 phage plaques, were chilled to 4° C. and plaques from each plate transferred onto two nitrocellulose filter circles by layering a dry filter on the agar plate for 5 min for the first filter and 15 min for the second filter. The filters were then placed on thick filter papers soaked in 0.2N NaOH, 1.5 M NaCl and 0.2% Triton X-100 for 5 min, and neutralized by layering onto filter papers soaked with 0.5M Tris-HCl pH 7.5 and 1.5M NaCl for another 5 min. The filters were washed in a similar fashion twice on filters soaked in 2×SSC (standard saline citrate), dried and then baked in a vacuum oven at 80° C. for 2 hrs. The duplicate filters were prehybridized at 55° C. for 4 hours with 10 ml per filter of DNA hybridization buffer (5×SSC) pH 7.0, 4×Denhardt's solution (polyvinylpyrrolidine, ficoll and bovine serum albumin, 1× =0.02% of each), 0.1% SDS, 50 mM sodium phosphate buffer pH 7.0 and 100 μg/ml of denatured salmon sperm DNA. $^{32}$P labelled probe was prepared by kinasing the oligonucleotide primer with $^{32}$P labelled ATP. The filters were hybridized to 3.5×10$^5$ cpm/ml of $^{32}$P labelled primer in 5 ml per filter of DNA hybridization buffer at 55° C. for 24 hours. The filters were washed at 55° C. for 30 min each in washing buffers containing 0.1% SDS and decreasing amount of SSC. The filters were washed initially with buffer containing 2×SSC and the control filters containing unmutated M13-β1 plaques were checked for the presence of any radioactivity using a Geiger counter. The concentration of SSC was lowered stepwise and the filters washed until no detectable radioactivity remained on the control filters with the unmutated M13-β1 plaques. The lowest concentration of SSC used was 0.1×SSC. The filters were air dried and autoradiographed at −70° C. for 2-3 days. 480 plaques of mutated M13-β1 and 100 unmutated control plaques were screened with the kinased oligonucleotide probe. None of the control plaques hybridized with the probe while 5 mutated M13-β1 plaques hybridized with the probe.

Figure 6:
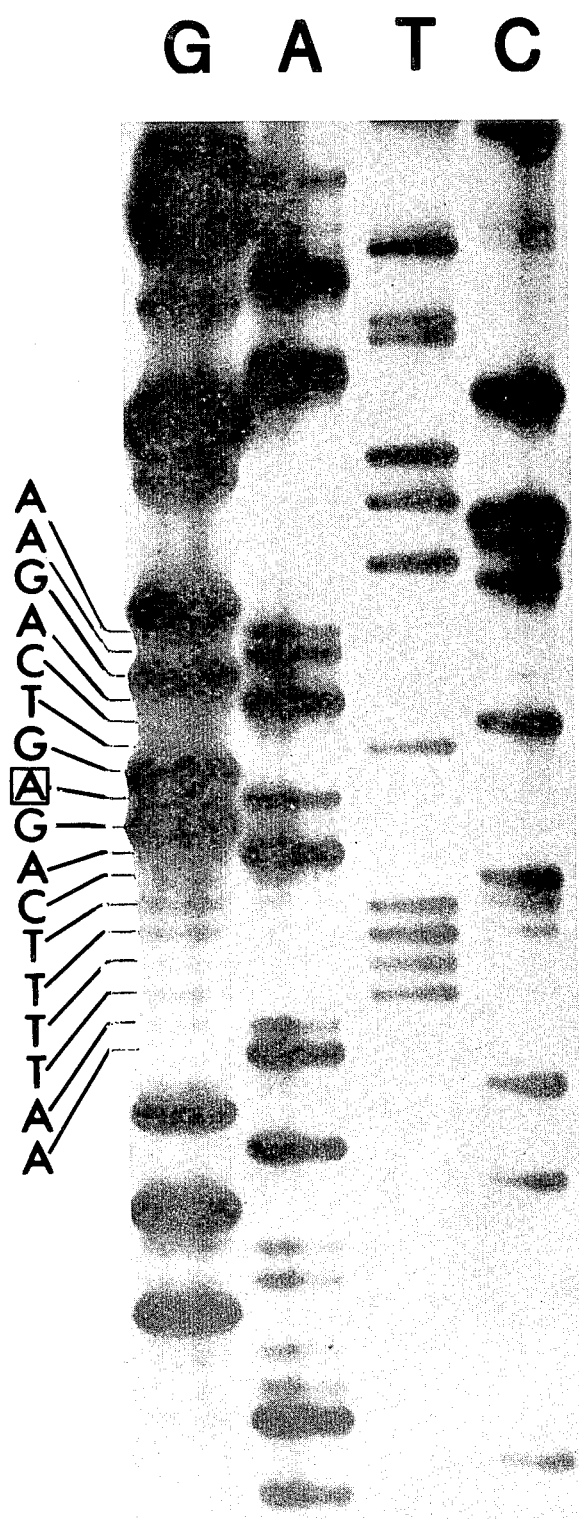
FIG. 6 shows the sequencing gel pattern of IFN-$\beta_{ser17}$ showing the single base change in the coding region.

One of the five mutated M13-β1 plaques (M13-SY2501) was picked and inoculated into a culture of JM103. Single-stranded DNA was prepared from the supernatant and double-stranded (ds) DNA was prepared from the cell pellet. The ssDNA was used as a template for the dideoxy-sequencing of the clone using the M13 universal primer. The result of the sequence analysis is shown in FIG. 6, confirming that the TAT cys codon has been converted to a AGT ser codon.

EXAMPLE 4

Figure 7:
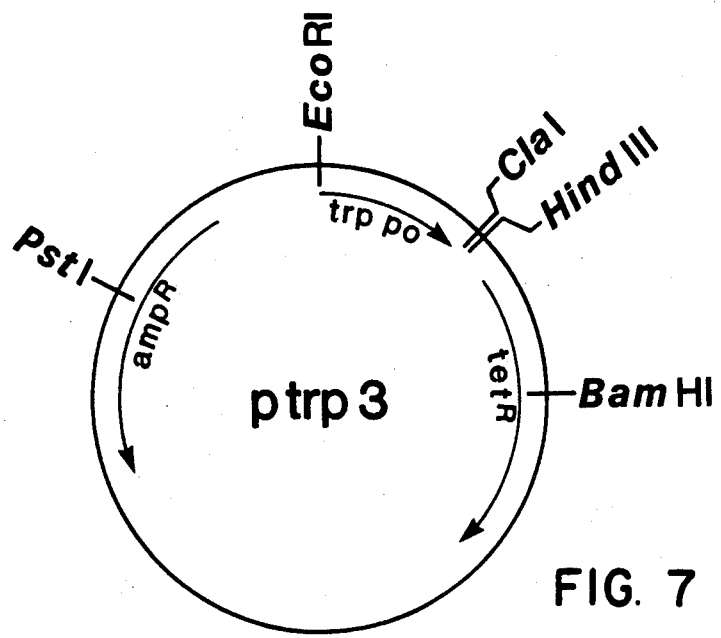
FIG. 7 is a diagram of the expression plasmid pTrp3.
Figure 9:
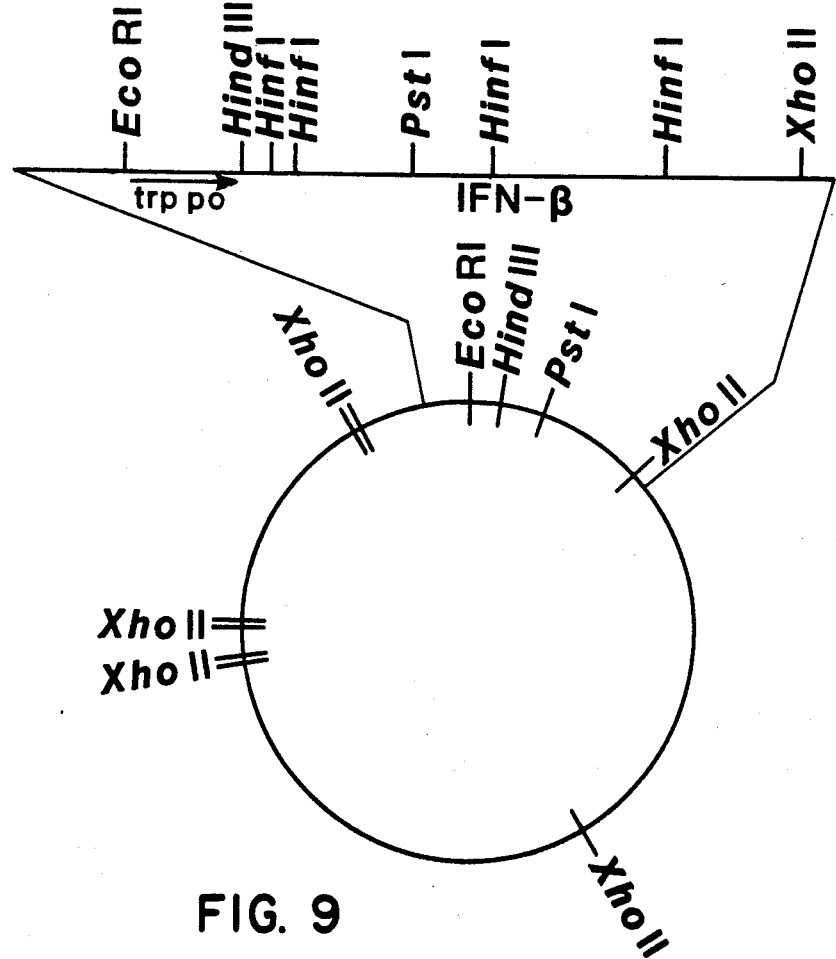
FIG. 9 is a restriction map of clone pSY2501.

Expression Of Mutated Interferon In E. Coli dsDNA from M13-SY2501 was digested with restriction enzymes HindIII and XhoII and the 520bp insert fragment purified on a 1% agarose gel. The plasmid pTrp3 containing the E. coli trp promoter (FIG. 7) was digested with the enzymes HindIII and BamHI, mixed with the purified M13-SY2501 DNA fragment, and ligated in the presence of T4 DNA ligase. The ligated DNA was transformed into E. coli strain MM294. Ampicillin resistant transformants were screened for sensitivity to the drug tetracycline. Plasmid DNA from five ampicillin resistant, tetracycline sensitive clones were digested with HinfI to screen for the presence of the M13-SY2501 insert. FIG. 8a shows the HinfI restriction pattern of one of the clones (pSY2501), comparing it with the HinfI pattern of the original IFN-β clone, pβ1trp. As expected, there is an additional HinfI site in pSY2501, cleaving the 197bp IFN-β internal fragment to a 169bp fragment and a 28bp fragment (FIG. 8b). A restriction map of clone pSY2501 is shown in FIG. 9. The complete DNA sequence of the serine-substituted IFN-β is shown in FIG. 10 together with the predicted amino acid sequence.

The plasmid designated as clone pSY2501 is on deposit with the Agricultural Research Culture Collection (NRRL), Fermentation Laboratory, Northern Regional Research Center, Science and Education Administration, U.S. Department of Agriculture, 1815 North University Street, Peoria, Ill. 61604 and is assigned accession numbers CMCC No. 1533 and NRRL No. B-15356.

Cultures of pSY2501 and pβ1trp were grown up to an $OD_{600}$ of 1.0. Cell free extracts were prepared and the amount of IFN-β antivirial activity assayed on GM2767 cells in a microtiter assay. Extracts of clone pSY2501 exhibited three to ten times higher activity than pβ1trp (Table 1), indicating that clone pSY2501 was either synthesizing more IFN-β protein or that the protein made had a higher specific activity.

TABLE I

| EXTRACT | ANTIVIRAL ACTIVITY (U/ml) |
| --- | --- |
| pSY2501 | $6 \times 10^5$ |
| pβ1trp | $1 \times 10^5$ |
| ptrp3 (control) | <30 |

Figure 11:
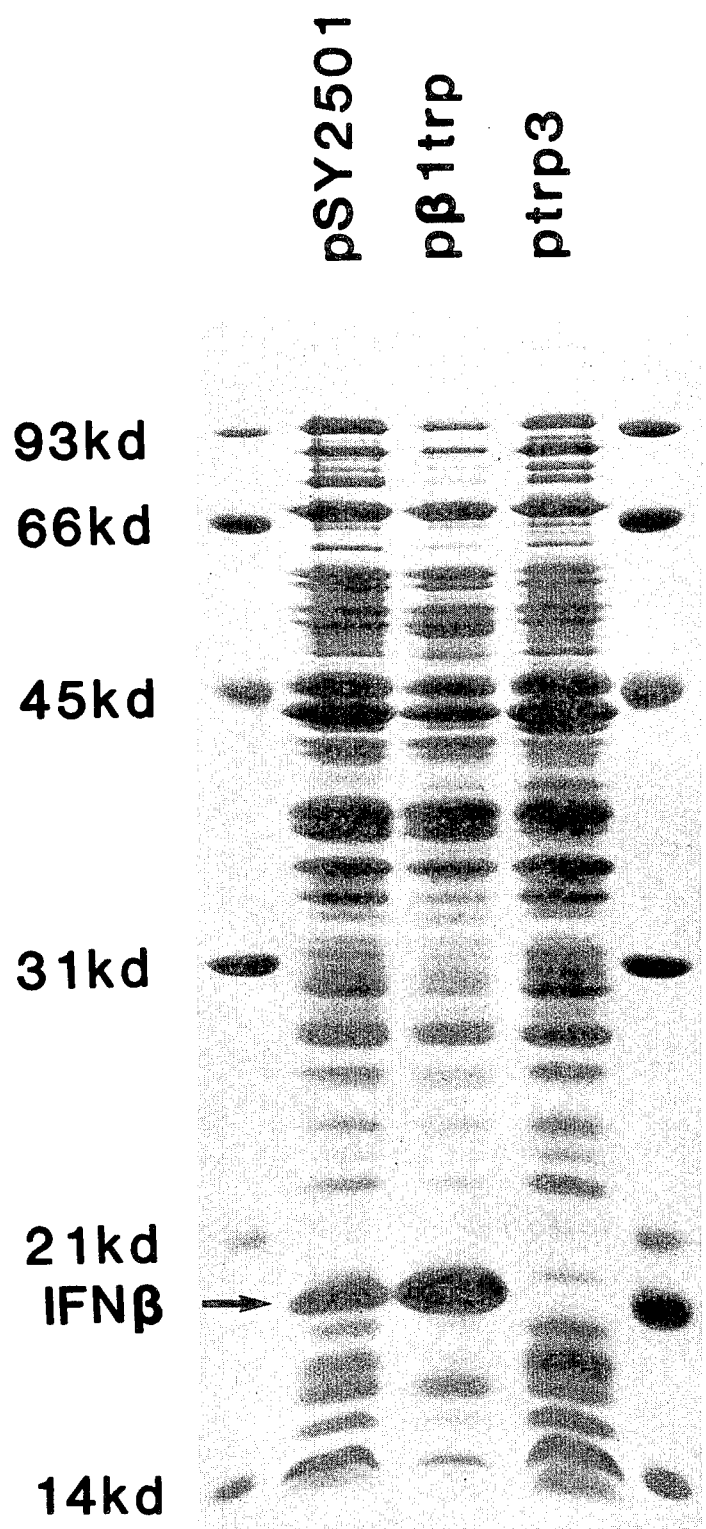
FIG. 11 shows the single 18,000 dalton protein band corresponding to IFN-$\beta_{ser17}$ in the extracts of clones pSY2501 and pβ1trp.

In order to determine if clone pSY2501 was synthesizing several times more IFN-β protein, the extracts of both clones were electrophoresed on a SDS polyacrylamide gel together with a control extract and the gel stained with coomasie blue to visualize the proteins. As shown in FIG. 11, there was only one protein band corresponding to an apparent 18,000 dalton protein that was present in the extracts of clones pSY2501 and pβ1trp but not in the control extract of ptrp3. This protein which has a molecular weight of about 20,000 daltons but shows a gel migration pattern of an 18,000 dalton protein, was previously shown to be IFN-β by purification of this protein from extracts of pβ1trp. Since there is less of this protein in extracts of pSY2501 than in extracts of pβ1trp, the specific activity of the protein in extracts of clone pSY2501 was higher than that of clone pβ1trp.

EXAMPLE 5

Purification Of IFN-β$_{ser17}$

The IFN-β$_{ser17}$ obtained from E. coli as described in Example 4 above was purified under both reducing and nonreducing conditions.

Purification Under Reducing Conditions

IFN-β$_{ser17}$ was recovered from E. coli that had been transformed to produce IFN-β$_{ser17}$. The E. coli were grown in the following growth medium to a cell density (OD) of 10–11 at 680 nm (dry wt 8.4 g/l).

| Ingredient | Concentration |
| --- | --- |
| NH$_4$Cl | 20 mM |
| K$_2$SO$_4$ | 16.1 mM |
| KH$_2$PO$_4$ | 7.8 mM |
| Na$_2$HPO$_4$ | 12.2 mM |
| MgSO$_4$.7H$_2$O | 3 mM |
| Na$_3$ citrate.2H$_2$O | 1.5 mM |
| MnSO$_4$.4H$_2$O | 30 μM |
| ZnSO$_4$.7H$_2$O | 30 μM |
| CuSO$_4$.5H$_2$O | 3 μM |
| L-tryptophan | 70 mg/l |
| FeSO$_4$.7H$_2$O | 72 μM |
| thiamine.HCl | 20 mg/l |
| glucose | 40 g/l | pH control with NH$_4$OH

A 9.9 l (9.9 kg) harvest of the transformed E. coli was cooled to 20° C. and concentrated by passing the harvest through a cross-flow filter at an average pressure drop of 16 psi and steady state filtrate flow rate of 260 ml/min until the filtrate weight was 8.8 kg. The concentrate (approximately one liter) was drained into a vessel and cooled to 15° C. The cells in the concentrate were then disrupted by passing the concentrate through a Manton-Gaulin homogenizer at 5° C., 10,000 psi. The homogenizer was washed with one liter phosphate buffered saline, pH 7.4 (PBS), and the wash was added to the disruptate to give a final volume of two liters. This volume was continuously centrifuged at 12000×g at a 50 ml/min flow rate. The solid was separated from the supernatant and resuspended in four liters PBS containing 2% by wt SDS. This suspension was stirred at room temperature for 15 min after which there was no visible suspended material. The solution was then extracted with 2-butanol at a 1:1 2-butanol:solution volume ratio. The extraction was carried out in a liquid-liquid phase separator using a flow rate of 200 ml/min. The organic phase was then separated and evaporated to dryness to yield 21.3 g of protein. This was resuspended in distilled water at a 1:10 volume ratio.

The recovered product was assayed for human IFN-β using an assay based on protection against viral cytopathic effect (CPE). The assay was made in microtiter plates. Fifty μl of minimum essential medium were charged into each well and 25 μl of the sample was placed in the first well and 1:3 volume dilutions were made serially into the following wells. Virus (vesicular stomatitis), cell (human fibroblast line GM-2767), and reference IFN-β controls were included on each plate. The reference IFN-β used was 100 units per ml. The plates were then irradiated with UV light for 10 min. After irradiation 100 μl of the cell suspension (1.2×10$^5$ cells/ml) was added to each well and the trays were incubated for 18–24 hr. A virus solution at one plaque-forming unit per cell was added to each well except the cell control. The trays were then incubated until the virus control shows 100% CPE. This normally occurs 18–24 hr after adding the virus solution. Assay results are interpreted in relation to the location of the 50% CPE well of the reference IFN-β control. From this point the titer of interferon for all samples on the plate are determined. The specific activity of the recovered product was determined to be 5×10$^7$ U/mg.

EXAMPLE 6

Alcohol Extraction

Partial purifications of IFN-β$_{ser17}$ using SDS as a solubilizing agent and 2-butanol as an extractant were made. Purifications using other alcohols were also attempted. The procedure used in these purifications was as follows.

The E. coli cells, 1.3 g (wet weight), were suspended in 10 ml of 1% SDS (wt/vol) in 0.1M PBS, pH 7.4. The suspension was sonicated until it was clear. An equal volume of extractant was added to the sonicate, mixed, and centrifuged at 7000×g for 10 min at ambient temperature. The extractant and aqueous phases were separated and the extractant phase was assayed for human IFN-β using the assay referred to in Example 5.

EXAMPLE 7

Acid Precipitation And Chromatographic Purification

The process of Example 5 was repeated except that after extraction and separation of the aqueous and organic phases and mixing of the organic phase with PBS at a volume ratio of 3:1 the pH of the mixture was lowered to about 5 by addition of glacial acetic acid. The resulting precipitate was separated by centrifugation at 10,000–17,000×g for 15 min and the pellet was redissolved in 10% w/v SDS, 10 mM DTT, 50 mM NaAcetate buffer, pH 5.5 and heated to 80° C. for 5 min.

The solution was then applied to a molecular sieve column with a Sephacryl S-200 Superfine (Pharmacia) matrix. The column was equilibrated with 50 mM sodium acetate buffer, pH 5.5 containing 2 mM dithiothreitol and 0.1%SDS (w/v) and 0.5 mM EDTA. The column was developed with the same buffer at a flow rate of 15.6 ml per cm$^2$ per hour. This procedure was repeated twice. Protein profile was monitored at 280 nm with a UV spectrophotometer. Fractions collected were assayed for protein content by the method of Lowry. Interferon concentration was determined by the CPE assay described in Example 5. Degree of interferon purity was determined by SDS polyacrylamide gel electrophoresis (Laemmle, Nature 1970). Fractions containing peak interferon activities were pooled, concentrated by ultrafiltration using an Amicon stir cell fitted with a PM10 membrane. Samples were applied to the G-75 Superfine column equilibrated with 50 mM NaAcetate buffer containing 0.1% SDS, 2 mM DTT and 0.5M EDTA and the column developed with the acetate/SDS/DTT/EDTA buffer at a flow rate of 3.0 ml to 6.0 ml per cm$^2$ per hour. Fractions containing highest interferon activities were pooled and the specific activity of the pooled interferon preparation was determined to be 9.0×10$^7$ to 3.8×10$^8$ international units per mg protein, as compared to about 2×10$^8$ U/mg for native IFN-β.

EXAMPLE 8

Purification Under Nonreducing Conditions

The procedure for the purification of IFN-β$_{ser17}$ under nonreducing conditions was the same as that described in Examples 6, 7 and 8 above except for the final chromatographic separation step in Example 8. The precipitate obtained, as described in Example 8, was dissolved in 10% SDS/50 mM sodium acetate buffer, pH 5.5. This solution was applied to a molecular sieve column packed with Sephacryl S-200 Superfine (Pharmacia) matrix. The column was equilibrated with 50 mM sodium acetate buffer, pH 5.5, containing 0.1% SDS (w/v). The column was developed with the same equilibrating buffer at a flow rate of 15.6 ml/cm$^2$ per hour. Fractions containing peak IFN-β$_{ser17}$ activity were concentrated by ultrafiltration using an Amicon stir cell fitted with a PM10 membrane.

The concentrate was then applied to a molecular sieve column with a Sephadex G-75 Superfine (Pharmacia) matrix. The column was equilibrated with 50 mM NaAcetate buffer, pH 5.5, containing 0.1% SDS.

The column was developed with a flow rate of 3.0 ml to 6.0 ml per cm$^2$ per hour with the same buffer.

Protein concentrations were determined both by the method of Lowry and by measuring extinction coefficients at 280 nm.

Antiviral activities were determined by an assay based on protection against viral catopathic effect as described in Example 5 above. Specific activity of the interferon preparations were determined to be 9.0×10$^7$ to 3.8×10$^8$ international units per mg protein.

EXAMPLE 9

Biochemical Characterization of IFN-β$_{ser17}$

Peak fractions from G-75 column chromatography chromatographed on a Aquapore RP8 column. All HPLC runs were done at ambient temperature (24–28° C.) in a Brownlee RP-300, 10 μm, "Aquapore" column using a Beckman gradient system. Buffer A was 0.1% TFA in H$_2$O; Buffer B was 0.1% TFA, 60% acetonitrile (CH$_3$CN) in H$_2$O. Detection was by absorbance at 214 nm, recorded at 0.2 absorbance units full scale. Injected samples contained 10–20 μg of IFN. The solvent program was as follows: 45 minutes linear gradient from 50% Buffer B (30% CH$_3$CN) to 100% Buffer B (60% CH$_3$CN); 5 minutes at 100% Buffer B; 15 minutes at 50% Buffer B; all at 1 ml/min. The collected fractions exhibited a symmetrical peak with a slight shoulder on the hydrophobic side. This was observed with samples purified either under reducing or nonreducing conditions. When identical samples were boiled with SDS and fresh DTT., the shoulder disappeared, resulting in a single symmetrical peak, indicating homogeneity of the protein sample. The IFN-β$_{ser17}$ thus obtained showed either a methionine or a serine residue as the first amino terminal amino acid, the NH$_2$-terminal serine containing species being the predominant.

The DNA sequences, coding for mature IFN-β, containing predetermined, site-directed mutations in codon 17, cloning vectors containing the DNA sequences, host organisms transformed with the vectors and methods therefor as described herein, yield an IFN-β$_{ser17}$ preparation which exhibits specific activity levels very close to that of native IFN-β. The IFN-β$_{ser17}$ thus obtained has no free sulfhydryl groups but indicates one —S—S bond between the only two cys at 31 and 141. The protein does not readily form oligomers and appears to be substantially in the monomeric form. The IFN-β$_{ser17}$ obtained in the various forms in accordance with this invention may be formulated either as a single product or mixtures of the various forms, into pharmaceutically acceptable preparations in inert, non-toxic, non-allergenic, physiologically compatible carrier media for clinical and therapeutic uses in cancer therapy and for viral infections. Such media include but are not limited to distilled water, physiological saline, Ringer's solution, Hank's solution and the like. Other nontoxic stabilizing and solubilizing additives such as HSA (human serum albumin) may be optionally included. The therapeutic formulations may be administered orally or parenterally such as intravenous, intramuscular, intraperitoneal and subcutaneous administrations.

The principal advantages of the instant invention lie in the elimination of a free sulfhydryl group at position 17, thereby forcing the protein to form correct disulfide links between cys 31 and cys 141 and to assume the conformation required for full biological activity. The increased specific activity of IFN-β$_{ser17}$ enables the use of smaller dosage in therapeutic uses. By deletion of the cysteine at position 17 and eliminating the free —SH group, the IFN-$\beta_{ser17}$ protein does not form dimers and oligomers so readily as the microbially produced IFN-$\beta$. This facilitates purification of the protein in that prior reduction and later reoxidation steps are eliminated thus increasing the yields of the protein product. Although the preferred embodiment described relates to the substitution of cys 17 by a serine, or threonine, other neutral amino acids such as glycine, alanine, valine, leucine, methionine, isoleucine, phenylalanine, tyrosine, histidine and tryptophan may also be used in the place of threo or ser.

The foregoing description of the preferred embodiments of the instant invention have been presented for purposes of illustration and description. It is not intended to be exhaustive or to limit the invention to the precise form disclosed, and obviously many modifications and variations are possible in the light of the above teaching. The particular embodiments were chosen and described in order to best explain the principles of the invention and its practical application to thereby enable others skilled in the art to best utilize the invention in various embodiments and with various modifications as are suited to the particular use comtemplated. It is intended that the scope of the invention be defined by the claims appended hereto.

What is claimed is:

1. A structural gene having a DNA sequence that encodes a synthetic IFN-$\beta$ wherein the cysteine residue at position 17, numbered in accordance with native human IFN-$\beta$, is replaced by a neutral amino acid.

2. The structural gene of claim 1 wherein the neutral amino acid is selected from the group consisting of serine, threonine, glycine, alanine, valine, leucine, isoleucine, histidine, tyrosine, phenylalanine, tryptophan, and methionine.

3. The structural gene of claim 1, wherein the neutral amino acid is serine or threonine.

4. The structural gene of claim 1, wherein the neutral amino acid is serine.

5. The structural gene of claims 1, 2, 3, or 4 with or without an initial ATG codon.

6. The structural gene as represented in FIG. 10, with or without the initial ATG codon.

7. An expression vector that includes that structural gene of claims 1, 2, 3 or 4.

8. The plasmid having an NRRL accession number B-15356.

9. A host cell transformed with an expression vector that includes a structural gene having a DNA sequence that encodes a synthetic IFN-$\beta$ wherein the cysteine residue at position 17, numbered in accordance with native human IFN-$\beta$, is replaced by a neutral amino acid and said mutein exhibits the biological activity of native human IFN-$\beta$, wherein the host cell is selected from the group consisting of bacteria, yeast, animal, and plant.

10. The host cell of claim 9, wherein the host cell is bacteria.

11. The host cell of claim 10, wherein the bacteria is E. coli.

12. The host cell of claims 9, 10 or 11, wherein the neutral amino acid is selected from the group consisting of serine, threonine, glycine, alanine, valine, leucine, isoleucine, histidine, tyrosine, phenylalanine, tryptophan, and methionine.

13. The host cell of claims 9, 10 or 11, wherein the neutral amino acid is serine.

14. E. coli transformed by an expression vector which includes the structural gene represented by FIG. 10, with or without the initial ATG codon.

15. E. coli transformed with the plasmid pSY2501 and progeny thereof.

* * * * *